United States Patent
Tachibana et al.

(10) Patent No.: US 9,849,436 B2
(45) Date of Patent: Dec. 26, 2017

(54) MICROFLUIDIC DEVICE

(71) Applicant: PANASONIC CORPORATION, Osaka (JP)

(72) Inventors: Hiroaki Tachibana, Osaka (JP); Eiichi Tamiya, Osaka (JP); Masato Saito, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 14/909,796

(22) PCT Filed: Mar. 10, 2014

(86) PCT No.: PCT/JP2014/001315
§ 371 (c)(1),
(2) Date: Feb. 3, 2016

(87) PCT Pub. No.: WO2015/019520
PCT Pub. Date: Feb. 12, 2015

(65) Prior Publication Data
US 2016/0199835 A1     Jul. 14, 2016

(30) Foreign Application Priority Data
Aug. 8, 2013 (JP) ................. 2013-165612

(51) Int. Cl.
*B01L 3/00* (2006.01)
*G01N 33/543* (2006.01)
(Continued)

(52) U.S. Cl.
CPC ..... *B01J 19/0093* (2013.01); *B01L 3/502715* (2013.01); *B01L 3/502746* (2013.01);
(Continued)

(58) Field of Classification Search
CPC .......... B01L 3/00; G01N 33/54; C12Q 1/683; C12Q 1/68
(Continued)

(56) References Cited

U.S. PATENT DOCUMENTS 4,775,515 A * 10/1988 Cottingham .......... B01L 3/5027
356/244
4,790,640 A * 12/1988 Nason ............... B01L 3/502707
156/99
(Continued)

FOREIGN PATENT DOCUMENTS

| JP | 2002-18271 | 1/2002 |
|---|---|---|
| JP | 2005-278418 | 10/2005 |

(Continued)

OTHER PUBLICATIONS

Kopp et al., "Chemical Amplification: Continuous-Flow PCR on a Chip", Science, vol. 280, May 15, 1998, pp. 1046-1048.
(Continued)

*Primary Examiner* — Arlen Soderquist
(74) *Attorney, Agent, or Firm* — Greenblum & Bernstein, P.L.C.

(57) ABSTRACT

A microfluidic device includes a channel through which a reaction solution flows. The channel passes through a reaction section having a plurality of temperature zones set at predetermined different temperatures. The channel includes, at least in the reaction section, a region where a cross-sectional area decreases in a feeding direction of the reaction solution.

15 Claims, 12 Drawing Sheets

(51) Int. Cl.
  *C12Q 1/68* (2006.01)
  *B01J 19/00* (2006.01)
  *B01L 7/00* (2006.01)

(52) U.S. Cl.
  CPC ......... *B01L 3/502761* (2013.01); *B01L 7/525* (2013.01); *C12Q 1/686* (2013.01); *G01N 33/54366* (2013.01); *B01J 2219/0084* (2013.01); *B01J 2219/0086* (2013.01); *B01J 2219/00831* (2013.01); *B01J 2219/00833* (2013.01); *B01J 2219/00849* (2013.01); *B01J 2219/00858* (2013.01); *B01J 2219/00873* (2013.01); *B01J 2219/00995* (2013.01); *B01L 2200/06* (2013.01); *B01L 2300/0627* (2013.01); *B01L 2300/0636* (2013.01); *B01L 2300/0816* (2013.01); *B01L 2300/0883* (2013.01); *B01L 2300/0887* (2013.01); *B01L 2300/18* (2013.01); *B01L 2300/1805* (2013.01); *B01L 2400/0406* (2013.01)

(58) Field of Classification Search
  USPC ..... 422/502, 129; 435/287.2, 303.2; 436/86, 436/165, 501
  See application file for complete search history.

(56) References Cited

U.S. PATENT DOCUMENTS

| | | | | |
|---|---|---|---|---|
| 5,019,351 | A * | 5/1991 | Schulz | B01L 3/502 356/244 |
| 5,707,799 | A * | 1/1998 | Hansmann | C08G 18/0866 422/417 |
| 6,180,372 | B1 * | 1/2001 | Franzen | B01L 3/502707 422/504 |
| 6,270,641 | B1 * | 8/2001 | Griffiths | B01F 5/0403 204/450 |
| 6,696,240 | B1 * | 2/2004 | Kloepfer | G01N 33/558 422/412 |
| 7,749,444 | B2 | 7/2010 | Yamada et al. | |
| 8,231,845 | B2 * | 7/2012 | Wyzgol | B01L 3/502746 422/412 |
| 8,414,847 | B2 * | 4/2013 | Davis | F04B 19/006 422/502 |
| 8,623,637 | B2 | 1/2014 | Ikeda | |
| 2004/0047767 | A1 * | 3/2004 | Bergman | B01L 3/502746 422/400 |
| 2005/0255007 | A1 | 11/2005 | Yamada et al. | |
| 2006/0228258 | A1 * | 10/2006 | Samsoondar | G01N 21/03 422/82.05 |
| 2007/0026421 | A1 * | 2/2007 | Sundberg | B01L 3/5027 435/6.12 |
| 2007/0287147 | A1 | 12/2007 | Nagamune et al. | |
| 2009/0162929 | A1 | 6/2009 | Ikeda | |

FOREIGN PATENT DOCUMENTS

| | | |
|---|---|---|
| JP | 2005-323519 | 11/2005 |
| JP | 2006-208188 | 8/2006 |
| JP | 2007-69164 | 3/2007 |
| JP | 2007-90306 | 4/2007 |
| JP | 2007-229631 | 9/2007 |
| JP | 2009-148232 | 7/2009 |
| JP | 2013-68546 | 4/2013 |
| WO | 2005/093420 | 10/2005 |
| WO | 2012/103533 | 8/2012 |

OTHER PUBLICATIONS

Burns et al., "An Integrated Nanoliter DNA Analysis Device", Science, vol. 282, October 16, 1998, pp. 484-487.
International Search Report, including English-langauge translation thereof, for PCT/JP2014/001315 dated Jun. 17, 2014.

* cited by examiner

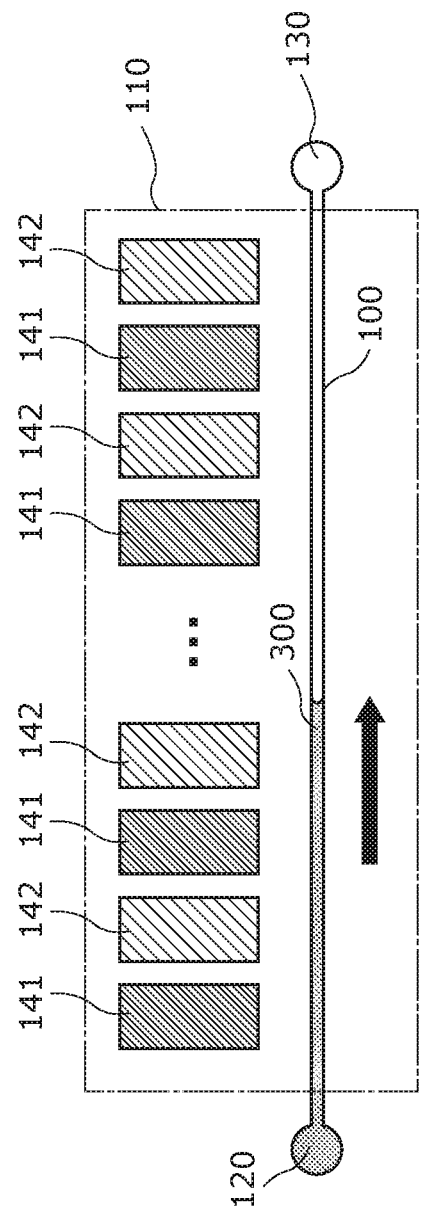

MICROFLUIDIC DEVICE

TECHNICAL FIELD

The present invention relates to a microfluidic device.

BACKGROUND ART

The microfluidic device is a device capable of inducing chemical reaction of a reaction solution including an extremely small amount of a sample and reagent, and examples include a microreaction device (microreactor), an integrated DNA device, and a microelectrophoresis device.

The microfluidic device is used in a reaction device that subjects the reaction solution to desired temperature changes. The temperature changes imparted on the reaction solution can be implemented rapidly with the use of a microfluidic device.

A nucleic acid amplification device that amplifies target nucleic acid by repeatedly imparting temperature changes is known. Using a microfluidic device as such a nucleic acid amplification device makes it possible to rapidly amplify the target nucleic acid.

For example, Patent Literature (PTL) 1 and Non Patent Literature (NPL) 1 disclose dividing a device into a plurality of different temperature zones and providing meandering channels that meander such that the reaction solution repeatedly passes through the temperature zones.

With this configuration, the reaction solution can be rapidly subjected to desired temperature changes simply by advancing the reaction solution through the meandering channel. With this, when a solution including nucleic acid is used as the reaction solution, nucleic acid amplification of the nucleic acid can be performed rapidly.

CITATION LIST

Patent Literature

[PTL 1] Japanese Unexamined Patent Application Publication No, 2002-18271

Non Patent Literature

[NPL 1] Science, vol. 280, pp. 1046-1048 (1998).

SUMMARY OF INVENTION

Technical Problem

However, with the above-described conventional microfluidic device, there is a problem that feeding the reaction solution at a constant speed is difficult, and making the time the reaction solution occupies each temperature zone constant is difficult.

In particular, when capillary force is used as the method of feeding the reaction solution, pressure loss of the reaction solution flowing through the channel increases with the feeding, whereby the feed velocity decreases with advancement of the fed reaction solution.

The present invention was conceived to solve the above-described problem and has an object to provide a microfluidic device that can feed a reaction solution at a constant speed.

Solution to Problem

In order to achieve the above-described object, according to one aspect of the present invention, a microfluidic device includes: a channel through which a reaction solution flows. The channel passes through a reaction section having a plurality of temperature zones set at predetermined different temperatures. The channel includes, at least in the reaction section, a region where a cross-sectional area decreases in a feeding direction of the reaction solution.

Moreover, in one aspect of the microfluidic device according to the present invention, in the region where the cross-sectional area decreases, the cross-sectional area of the channel may monotonically decrease.

Moreover, in one aspect of the microfluidic device according to the present invention, in the region where the cross-sectional area decreases, the channel may have a tapered structure.

Moreover, in one aspect of the microfluidic device according to the present invention, in the region where the cross-sectional area decreases, the channel may have a tapered width and a constant depth.

Moreover, in one aspect of the microfluidic device according to the present invention, in the region where the cross-sectional area decreases, the cross-sectional area of the channel may decrease in a step-wise fashion.

Moreover, in one aspect of the microfluidic device according to the present invention, in the region where the cross-sectional area decreases, the channel may include a plurality of lines arranged in a meandering fashion, and in the region where the cross-sectional area decreases, the cross-sectional area of the channel may decrease with each line in the feeding direction.

Moreover, in one aspect of the microfluidic device according to the present invention, in the region where the cross-sectional area decreases, the channel may have a narrower width with each line and a constant depth.

Moreover, in one aspect of the microfluidic device according to the present invention, the region where the cross-sectional area decreases may be the entire portion of the channel in the reaction section.

Moreover, in one aspect of the microfluidic device according to the present invention, in the region where the cross-sectional area decreases, the cross-sectional area of the channel may be adjusted with a pillar disposed in the channel.

Moreover, in one aspect of the microfluidic device according to the present invention, the channel may be a meandering channel arranged to pass back and forth through the plurality of temperature zones, and the reaction solution may be subjected to cyclic temperature changes by being fed through the meandering channel.

Moreover, in one aspect of the microfluidic device according to the present invention, the reaction solution may include a target nucleic acid, and the target nucleic acid may be amplified by a polymerase chain reaction as a result of the reaction solution passing through the reaction section of the channel.

Moreover, in one aspect of the microfluidic device according to the present invention, the reaction solution may include one of a bacteria and virus as an analyte, and the microfluidic device may detect the analyte included in the reaction solution.

Moreover, in one aspect of the microfluidic device according to the present invention, an antibody that specifically reacts with the analyte may be immobilized in the channel.

Moreover, in one aspect of the microfluidic device according to the present invention, a portion of the channel may be divided into branches.

Moreover, in one aspect of the microfluidic device according to the present invention, the channel may be formed in a substrate, and the substrate may include one of silicon, resin, and glass.

Advantageous Effects of Invention

According to the present invention, since the reaction solution can be fed at a constant velocity, the time the reaction solution occupies each temperature zone can be made constant.

BRIEF DESCRIPTION OF DRAWINGS

FIG. 5 is for illustrating the temperature cycle in a microfluidic device according to an embodiment of the present invention.

DESCRIPTION OF EMBODIMENTS

Figure 1:
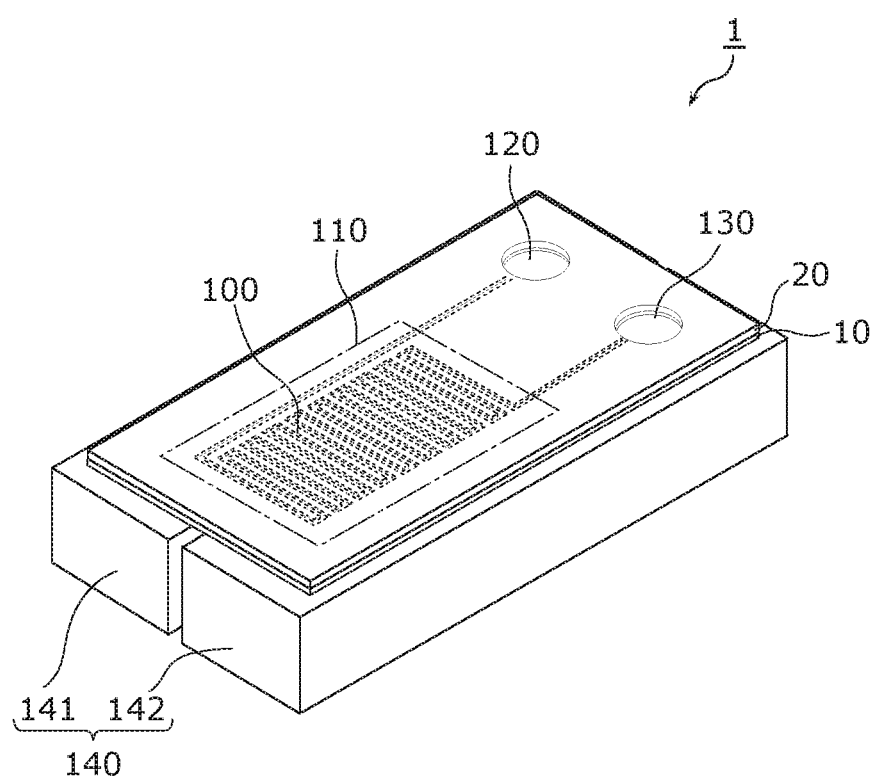
FIG. 1 is a schematic perspective view of a microfluidic device according to an embodiment of the present invention.

Hereinafter, embodiments of present invention are described with reference to the Drawings. Note that the exemplary embodiment described below shows a specific preferred example of the present disclosure. Therefore, the numerical values, shapes, materials, elements, arrangement and connection of the elements, steps, order of the steps, etc., shown in the following embodiments are mere examples, and are not intended to limit the present invention. Consequently, among the structural elements in the following embodiments, elements not recited in any one of the independent claims which indicate the broadest concepts of the present disclosure are described as arbitrary structural elements.

It should be noted that the respective figures are schematic diagrams and are not necessarily precise illustrations. Additionally, components that are essentially the same share the same reference numerals in the respective figures, and overlapping explanations thereof are omitted or simplified.

(Embodiment)

Figure 2:
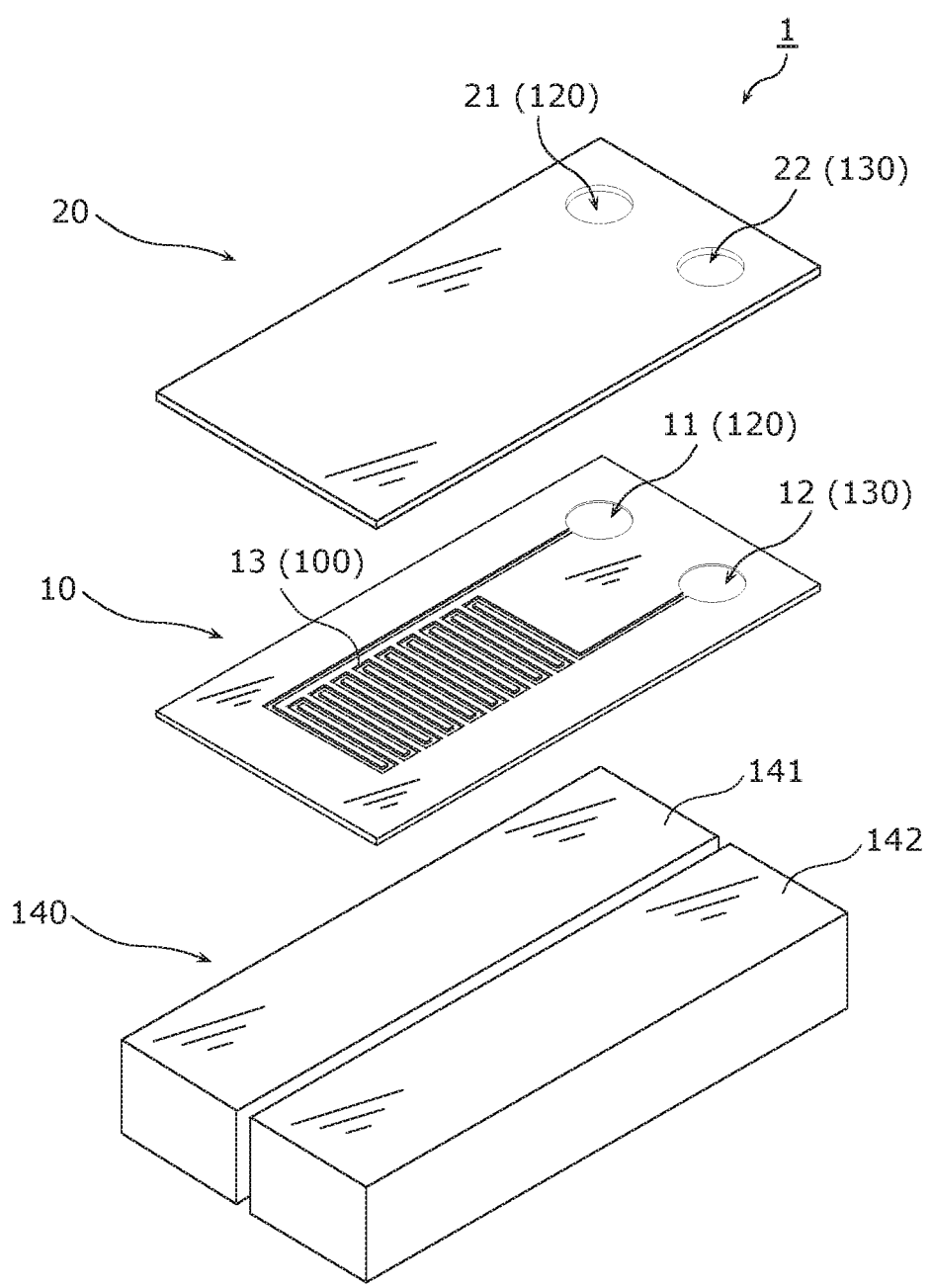
FIG. 2 is an exploded perspective view of a microfluidic device according to an embodiment of the present invention.
Figure 3:
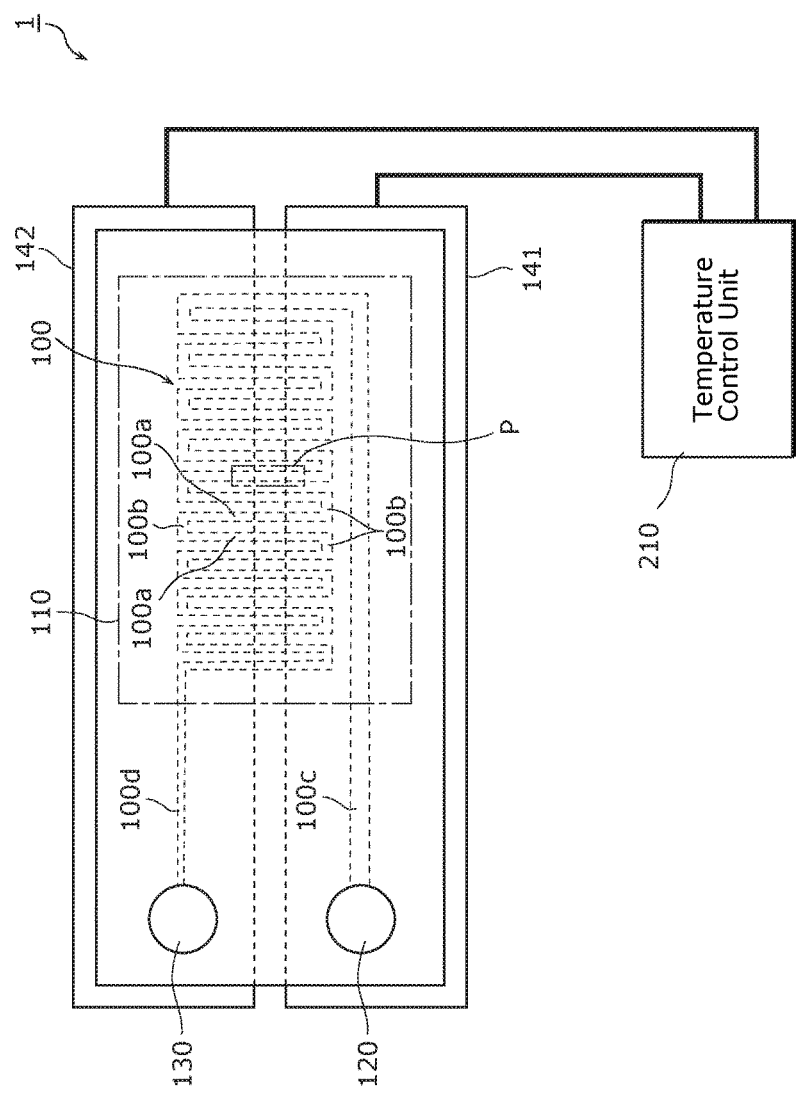
FIG. 3 is a plan view of a microfluidic device according to an embodiment of the present invention.
Figure 4:
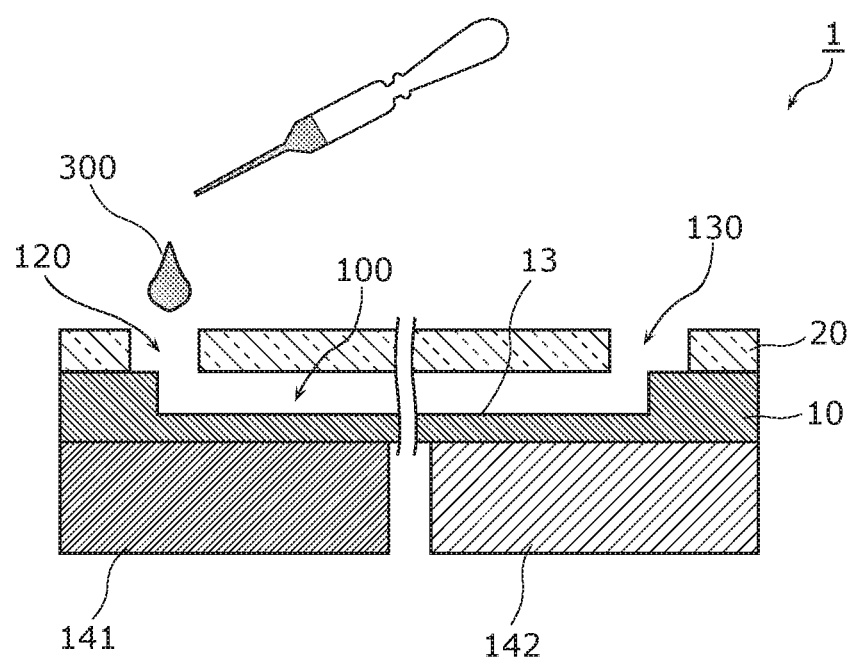
FIG. 4 is a cross sectional view of a microfluidic device according to an embodiment of the present invention.

The configuration of the microfluidic device 1 according to Embodiment 1 of the present invention will be described using FIG. 1 through FIG. 4. FIG. 1 is a schematic perspective view of the microfluidic device according to an embodiment of the present invention, FIG. 2 is an exploded perspective view of the same microfluidic device, FIG. 3 is a plan view of the same microfluidic device, and FIG. 4 is a cross sectional view of the same microfluidic device.

As illustrated in FIG. 1 through FIG. 4, the microfluidic device 1 according to the present embodiment is a device (microchip) including a channel 100 through which a reaction solution flows.

The channel 100 is a reaction channel through which the reaction solution flows one-way, and passes through at least a reaction section 110 having a plurality of temperature zones set at predetermined different temperatures. At least the portion of the channel 100 in the reaction section 110 includes a region having a cross-sectional area that decreases in the feeding direction of the reaction solution.

The reaction section 110 is a region for inducing a chemical reaction of the reaction solution. In the present embodiment, the reaction solution is a solution including a target nucleic acid sample, and more specifically, is an aqueous solution including the target nucleic acid and a reagent for amplifying the target nucleic acid. As such, the reaction section 110 according to the present embodiment is a nucleic acid amplification reaction section, and the target nucleic acid included in the reaction solution is amplified in the reaction section 110. Note that the reaction solution may include, for example, some type of alcohol or a surfactant.

In this way, the microfluidic device 1 according to the present embodiment is used as a nucleic acid amplification device for amplifying a sample of a target nucleic acid. The polymerase chain reaction (PCR) method will be used with the microfluidic device 1 in the example given hereinafter. The PCR method is a technique of amplifying DNA with a temperature cycle. In addition to the target DNA, the reaction solution (reaction fluid) includes, for example, a PCR primer, a polymerase enzyme, and a buffer. Subjecting this sort of reaction solution to a temperature cycle makes it possible to amplify the DNA. The amount of amplification of the amplified DNA can be detected by a reaction detection mechanism.

The microfluidic device 1 embodied as a nucleic acid amplification device includes an introduction unit (inlet) 120 into which the reaction solution including the target nucleic acid is introduced, the reaction section 110 for amplifying the target nucleic acid included in the reaction solution introduced into the introduction unit 120, a discharge unit (drain) 130 for discharging the reaction solution including the target nucleic acid amplified in the reaction section 110, and a heater unit 140 for heating the reaction solution including the target nucleic acid.

More specifically, the microfluidic device 1 is configured of a first substrate 10, a second substrate 20, and the heater unit 140. Moreover, the heater unit 140 includes a first heater block 141 and a second heater block 142 which have different set temperatures. The silhouette of the microfluidic device 1 according to the present embodiment is, for example, a 40 mm long by 20 mm wide approximate rectangle.

Hereinafter, each element in the microfluidic device 1 will be described in detail using FIG. 1 through FIG. 4.

[First Substrate]

As illustrated in FIG. 2, the first substrate 10 includes a first recessed portion 11 that forms part of the introduction unit 120, a second recessed portion 12 that forms part of the discharge unit 130, and a groove 13 that forms the channel 100. A silicon substrate, for example, can be used as the first substrate 10.

The groove 13 (the channel 100) is formed so as to connect the first recessed portion 11 and the second recessed portion 12. The reaction solution flows in the groove 13 (the channel 100). More specifically, when the reaction solution is introduced into the first recessed portion 11 (the introduction unit 120), the reaction solution advances through the groove 13 (the channel 100) toward the second recessed portion 12 (the discharge unit 130).

As illustrated in FIG. 3, the channel 100 is a meandering channel formed so as to meander in such a manner as to alternately pass through the first heater block 141 (the first temperature zone) and the second heater block 142 (the second temperature zone) repeatedly.

More specifically, the portion of the channel 100 in the reaction section 110 is formed so as to continuously bend back on itself (run back and forth) at bends located at predetermined intervals in the line-shaped channel. The number of times the portion of the channel 100 in the reaction section 110 bends back on itself is equivalent to about 20 to 70 cycles. Note that, as one example, the length of the channel 100 per cycle (the length of one main channel 100*a*) can be 32 mm.

The channel 100 according to the present embodiment includes a plurality of line-shaped main channels 100*a* of a predetermined length and sub channels 100*b* that connect two ends adjacent rows of the main channels 100*a*. The main channels 100*a* and the sub channels 100*b* are disposed in the reaction section 110.

The main channels 100*a* are disposed approximately perpendicular to the lengthwise direction of the first heater block 141 and the second heater block 142 in such a manner as to bridge the first heater block 141 and the second heater block 142. The sub channels 100*b* are disposed approximately parallel to the lengthwise direction of the first heater block 141 and the second heater block 142.

Note that the channel 100 further includes an introduction channel 100*c* that is a channel for guiding the reaction solution from the introduction unit 120 to the reaction section 110, and a discharge channel 100*d* for guiding the reaction solution from the reaction section 110 to the discharge unit 130.

The starting end of the introduction channel 100*c* is the entrance for the entire channel 100, and the terminal end of the introduction channel 100*c* is the entrance for the portion of the channel 100 in the reaction section. The starting end of discharge channel 100*d* is the exit for the portion of the channel 100 in the reaction section, and the terminal end of the discharge channel 100*d* is the exit for the entire channel 100.

Note that in the present embodiment, a silicon oxide film is formed on the inner surface of the groove 13 forming the channel 100. Forming the silicon oxide film makes the wall surface of the channel 100 (the groove 13) hydrophilic. In the present embodiment, the silicon oxide film is formed on each of the main channels 100*a*, the sub channels 100*b*, the introduction channel 100*c*, and the discharge channel 100*d*.

The channel 100 configured in this way is a micro channel, and, for example, has a rectangular cross sectional shape. In this case, the channel width (groove width) of the groove 13 forming the channel 100 is, for example, about 20 to 300 μm, and the depth of the groove 13 is about 50 to 150 μm.

Note that the cross sectional shape of the groove 13 is not limited to a rectangular shape, and may be a semicircle or inverted triangle. Moreover, the first recessed portion 11 and the second recessed portion 12 can be recessed portions having circular openings, for example. Note that the material of the first substrate 10 is not ited to silicon, and may be resin or glass, for example.

[Second Substrate]

As illustrated in FIG. 1, the second substrate 20 is a lid that covers the first substrate 10 and is disposed on the first substrate 10. A glass substrate, for example, can be used as the second substrate 20.

As illustrated in FIG. 2, the second substrate 20 includes, as part of the introduction unit 120, a first through-hole 21 that opens through the second substrate 20. The second substrate 20 also includes, as part of the discharge unit 130, a second through-hole 22 that opens through the second substrate 20. The first through-hole 21 and the second through-hole 22 are through-holes having, for example, a circular opening.

By placing the second substrate 20 on the first substrate 10, the opening of the groove 13 is sealed whereby the channel 100 is sealed in all directions. With this, the wall surfaces of the channel 100 enclose an entire perimeter of the channel 100 in a cross section taken perpendicular to the feeding direction (traveling direction) of the reaction solution, and the channel 100 is connected to an external space only in the introduction unit 120 and the discharge unit 130. Here, by enclosing the channel 100 in all directions, the reaction solution can be inhibited from volatilizing while being fed.

Note that the material of the second substrate 20 is not limited to glass, and may be resin or silicon, for example.

[Heater Unit]

As illustrated in FIG. 1 through FIG. 3, the heater unit 140 is disposed in at least the reaction section 110, and the reaction solution fed through the portion of the channel 100 in the reaction section 110 is subjected to a predetermined temperature by the heater unit 140.

In the present embodiment, as the heater unit 140, the first heater block 141 and the second heater block 142, which are set at predetermined different temperatures, are located in the reaction section 110. In other words, the two heater blocks—the first heater block 141 and the second heater block 142—form two temperature zones set at predetermined different temperatures in the reaction section 110.

Note that the first heater block 141 and the second heater block 142 are, for example, heaters using cuboid blocks of metal such as aluminum or stainless steel. Other than heater blocks, metal thin film heaters formed by printing a metal thin film on a glass substrate, for example, can be used as the heater unit 140.

The region in which the first heater block 141 set at a first temperature is located is a first temperature zone. The region in which the second heater block 142 set at a second temperature is located is a second temperature zone different from the first temperature zone.

In the present embodiment, the temperature of the first heater block 141 is set higher than the temperature of the second heater block 142. In other words, the region in which the first heater block 141 is located is a high temperature zone, and the region in which the second heater block 142 is located is a low temperature zone.

The temperature of the first heater block 141, which is the high temperature zone, is, for example, 93° C. to 98° C., and in the present embodiment, is set to approximately 95° C., which is the temperature at which denaturation of the nucleic acid amplification reaction occurs. The temperature of the second heater block 142, which is the low temperature zone, is, for example, 50° C. to 75° C., and in the present embodiment, is set to approximately 60° C., which is the temperature at which annealing and extension occurs.

As illustrated in FIG. 3, the heater unit 140 is connected to a temperature control unit 210. With this, the temperatures of the first heater block 141 and the second heater block 142 can be controlled by the temperature control unit 210.

The first heater block 141 and the second heater block 142 are lined up with a predetermined space between them. The first substrate 10 is disposed on the first heater block 141 and the second heater block 142. More specifically, the first substrate 10 is placed on the heater unit 140 so that the main channels 100a of the channel 100 bridge the first heater block 141 and the second heater block 142. With this, the channel 100 is configured to pass back and forth through the two temperature zones in a plurality of cycles.

With this configuration, as illustrated in FIG. 5, when the reaction solution 300 is introduced via the introduction unit 120, the reaction solution 300 is fed to the discharge unit 130 in such a manner as to alternately pass through the two temperature zones (the first heater block 141 and the second heater block 142) in the reaction section 110 repeatedly. In other words, the reaction solution 300 flowing through the channel 100 can be subjected to a heat cycle.

Next, the nucleic acid amplification method using the microfluidic device 1 according to an embodiment of the present invention will be described using FIG. 1 through FIG. 4.

First, as illustrated in FIG. 4, a pipette is used to dispense the reaction solution 300 into the introduction unit 120. In the present embodiment, a premixed solution including the reagent and the reaction solution, which includes the target nucleic acid, is introduced into the introduction unit 120 of the microfluidic device 1 as the reaction solution.

The reaction solution 300 introduced into the introduction unit 120 is fed from the introduction unit 120 to the reaction section 110 via the channel 100 (the introduction channel 100c).

As illustrated in FIG. 3, the reaction solution reaching the reaction section 110 repeatedly passes back and forth through the first heater block 141 and the second heater block 142 as it passes through the main channels 100a and the sub channels 100b. In other words, since the reaction solution passes back and forth through the high temperature zone (the first heater block 141) and the low temperature zone (the second heater block 142) of the heater unit 140 as it is fed, the reaction solution is alternately and repeatedly heated and cooled. With this, the target nucleic acid included in the reaction solution is amplified as a result of repeated denaturation in the high temperature zone and annealing and extension in the low temperature zone. In this way, since the temperature of the reaction solution can be increased and decreased as the reaction solution is fed, substantially rapid PCR by flow can be achieved. Thus, the target nucleic acid included in the reaction solution can be rapidly amplified.

Next, the reaction solution is fed from the reaction section 110 to the discharge unit 130 via the discharge channel 100d. In the present embodiment, when the fluid front of the reaction solution introduced into the introduction unit 120 reaches the discharge unit 130, introduction of the solution including the target nucleic acid (referred to as the reaction solution in the present embodiment) into the introduction unit 120 is interrupted, which results in the channel 100 being filled with the reaction solution. Note that the reaction solution reaching the discharge unit 130 may be discharged from the discharge unit 130 as needed.

In this way, the reaction solution advances through the channel 100. Note that in the present embodiment, the channel 100 includes a hydrophilic wall surface with an acute contact angle θ as the capillary force transport mechanism that feeds the reaction solution by capillary force. More specifically, the silicon oxide film is formed on the three wall surfaces—the bottom surface and both side surfaces—of the groove 13 in a cross section taken perpendicular to the feeding direction of the reaction solution 300. Forming the silicon oxide film makes the surfaces of the groove 13 hydrophilic, giving the inner wall surfaces of the channel 100 a hydrophilic surface.

With this, since self-propelled flow of the reaction solution in the channel 100 is achieved by capillary forces acting at the air-water interface, the reaction solution automatically advances through the channel 100. In other words, the reaction solution is subjected to cyclic temperature changes in the reaction section 110 as the reaction solution is fed through the channel 100 by automated transport.

Note that only a portion of the wall surfaces of the channel 100 is required have a hydrophilic surface, but wall surfaces around the entire perimeter of the channel 100 in a cross section taken perpendicular to the feeding direction are preferably hydrophilic surfaces. In this case, in addition to the surfaces of the groove 13 of the first substrate 10, the surface of the second substrate 20 (the inner surface) may be made to be hydrophilic. Note that the greater the percentage of the wall surface in the cross section of the channel 100 is hydrophilic, the greater the capillary force applied to the reaction solution.

Next, feed velocity when the reaction solution is fed through the channel 100 by capillary force will be described.

First, the theory behind using capillary force in the channel 100 will be described.

Feeding liquid using capillary force is determined by the balance between capillary force, which is the driving force, and pressure loss, which is the resistance component. Here, pressure loss $P_d$ can be represented as illustrated in (Expression 1) below.

[Math 1]

$$P_d = \frac{128 Q \eta l}{\pi D_h^4} \quad \text{(Expression 1)}$$

In (Expression 1), Q represents amount of flow, η represents viscosity of the solution, and l represents channel length. Moreover, in (Expression 1), Dh is the hydraulic diameter defined by (Expression 2) below, and is a parameter that reflects the size and shape of the channel.

[Math 2]

$$D_d = \frac{4S}{U} \quad \text{(Expression 2)}$$

In (Expression 2), S represents channel cross-sectional area, and U represents outer circumference length of the channel cross section.

(Expression 1) can be rewritten as (Expression 3) below by using feed velocity v and channel cross-sectional area S, and further inserting pressure loss coefficient α.

[Math 3]

$$P_d = \frac{128 S v \eta l}{\pi D_h^4} = \alpha \times l \times v \quad \text{(Expression 3)}$$

(Expression 3) illustrates that pressure loss $P_d$ is proportionate to channel length l and feed velocity v when a solution is fed through the channel.

Here, from the balance between pressure loss $P_d$ in (Expression 3) and capillary force Pc ($P_d = P_c$), feed velocity v achieved by capillary force $P_c$ can be represented by (Expression 4) below.

[Math 4]

$$v = \frac{P_c}{\alpha} \times \frac{1}{l} \quad \text{(Expression 4)}$$

In (Expression 4), $P_c/\alpha$ is a constant determined by the size and shape of the channel and the type of solution used, and here is defined as the feed coefficient and is used as an indicator of capillary force feeding characteristics.

The feed velocity v achieved by capillary force $P_c$ is a proportionality constant of the feed coefficient, and is inversely proportional to channel length l, that is to say, to the feed distance.

Moreover, since (Expression 4) is a differential equation of time t and feed distance (channel length l), by solving (Expression 4), feed distance l relative to time t is expressed as shown in (Expression 5) below, and is proportional to the square root of time t.

[Math 5]

$$l = \sqrt{2 \frac{P_c}{\alpha} t} \quad \text{(Expression 5)}$$

In (Expression 5), which determines the feeding characteristics, pressure loss coefficient α is a significantly meaningful parameter.

Next, capillary force $P_c$ will be described in detail. Capillary force $P_c$ can be represented as a sum of the interfacial tensions of each side in the channel cross section, and can be expressed as (Expression 6) below.

[Math 6]

$$P_c = \frac{\sigma}{S} \sum_n a_n \cos\theta_n \quad \text{(Expression 6)}$$

In (Expression 6), σ represents surface tension of the solution, S represents channel cross-sectional area, and $a_n$ and $\theta_n$ represent the length of the sides in the channel cross section and contact angle, respectively. For example, when the channel has a rectangular cross section, capillary force $P_c$ is expressed as shown in (Expression 7).

[Math 7]

$$P_c = \sigma \left( \frac{\cos\theta_l + \cos_r}{w} + \frac{\cos\theta_l + \cos_b}{d} \right) \quad \text{(Expression 7)}$$

Here, w and d represent the width and the depth of the channel, respectively, and $\theta_l$, $\theta_r$, $\theta_t$, and $\theta_b$, represent the contact angle of the left wall surface (left surface) of the channel, the contact angle of the right wall surface (right surface) of the channel, the contact angle of the top wall surface (top surface) of the channel, and the contact angle of the bottom wall surface (bottom surface) of the channel, respectively.

With the microfluidic device 1 according to the present embodiment, the reaction solution continuously flows through regions of different temperature and shape. Therefore, there is a need to construct a theory regarding feeding that can accommodate any given temperature and shape.

Suppose a solution (liquid) is fed through a given channel by capillary force $P_c$, and the fluid front is at point x=l. Since capillary force Pc is only associated with the fluid front of the fed solution, capillary force $P_c$ is represented by (Expression 6), and x=l is determined by the shape and temperature of the channel.

On the other hand, since pressure loss $P_d$ is associated with the entire region from point x=0 to point x=l, (Expression 3) needs to be expanded and considered as (Expression 8) below. In (Expression 8), pressure loss coefficient α is a constant determined by the temperature and shape at a given point x.

[Math 8]

$$P_d = \int_0^l \alpha dx \times v \quad \text{(Expression 8)}$$

Here, one can consider feed velocity v in a channel designed for PCR by flow to be determined by (Expression 9) below from the balance between pressure loss $P_d$ in (Expression 8) and capillary force Pc ($P_d = P_c$).

[Math 9]

$$v = \frac{P_c}{\int_0^l \alpha \, dx} \quad \text{(Expression 9)}$$

(Expression 9) is the same as (Expression 4) except for the fact that the denominator to the right is an integral.

With this, feed velocity v (flow speed) can be calculated from capillary force $P_c$ and pressure loss coefficient α.

[Characteristics and Operational Advantages]

Figure 6A:
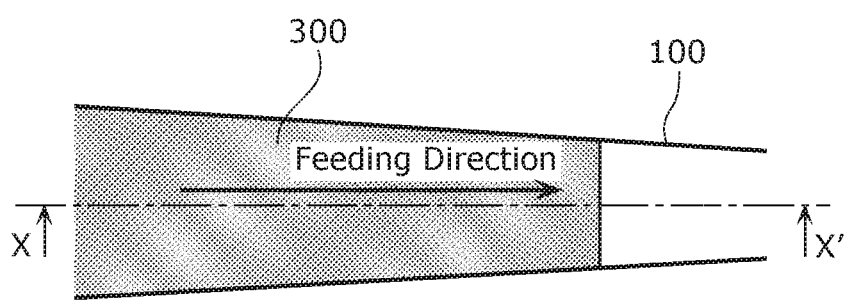
FIG. 6A is an enlarged plan view of a relevant section of a channel in a microfluidic device according to an embodiment of the present invention.
Figure 6B:
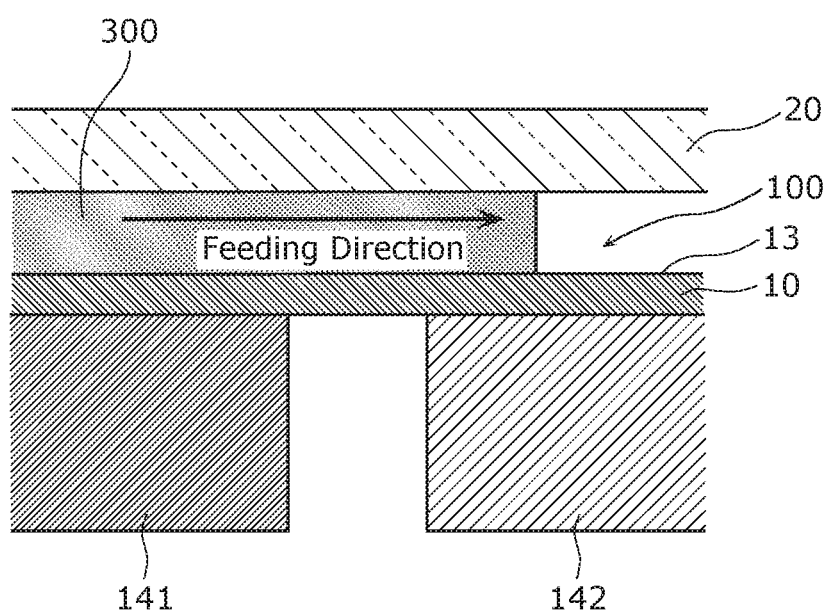
FIG. 6B is a cross sectional view of a channel in a microfluidic device according to an embodiment of the present invention, taken at line X-X' in FIG. 6A.
Figure 7:
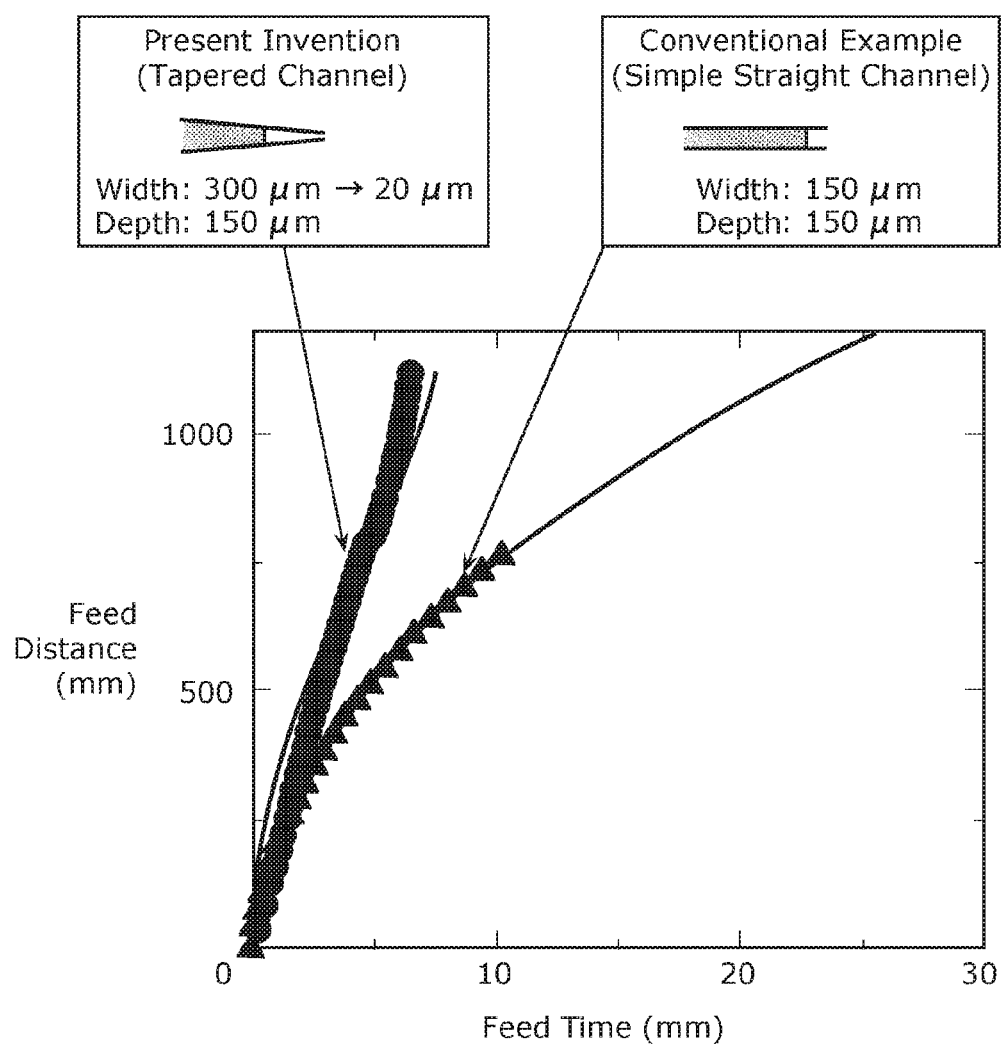
FIG. 7 illustrates the dependency between feed time and feed distance of a reaction solution in a microfluidic device according to an embodiment of the present invention.

The characteristics and operational advantages of the microfluidic device 1 according to an embodiment of the present invention will be described using FIG. 6A, FIG. 6B, and FIG. 7. FIG. 6A is an enlarged plan view of a relevant section of the channel in the microfluidic device according to an embodiment of the present invention, and is an enlarged view of section P encompassed by a solid line in FIG. 3. FIG. 6B is a cross sectional view of the channel in the microfluidic device according to an embodiment of the present invention, taken at line X-X' in FIG. 6A, FIG. 7 illustrates the dependency between feed time and feed distance of the reaction solution in the microfluidic device according to an embodiment of the present invention. Note that in FIG. 7, the round black dots and the black triangles represent actual measurement values for their respective channel structures, and the solid line and the curved line represent simulation values for their respective channel structures.

As illustrated in FIG. 6A and FIG. 6B, in the microfluidic device 1 according to the present embodiment, the channel 100 includes, in at least the reaction section 110 (i.e., the main channels 100a and the sub channels 100b include), a region where the cross-sectional area decreases in the feeding direction of the reaction solution 300.

In the present embodiment, in the region where the cross-sectional area decreases, the channel cross-sectional area of the channel 100 monotonically decreases. More specifically, in the region where the cross-sectional area decreases, the channel 100 has a tapered structure where the width of the channel 100 is tapered and the depth of the channel 100 is constant along the feeding direction. In other words, from upstream to downstream, the width of the channel 100 gradually decreases.

With such a channel 100, the feed distance of the reaction solution is proportional to the feed time of the reaction solution, as illustrated in FIG. 7 ("Present Invention" in FIG. 7). In other words, the feed velocity of the reaction solution can be maintained at a constant velocity. Note that in FIG. 7, a channel having a constant depth of 150 μm and a width that gradually narrows from 300 μm to 20 μm is used as the tapered channel labeled as "Present Invention".

On the other hand, with the conventional channel that has a constant channel cross-sectional area ("Conventional Example" in FIG. 7), the reaction solution is not fed at a constant velocity, and thus the distance per unit time that the reaction solution is fed gradually decreases, as illustrated in FIG. 7. Note that in FIG. 7, a channel having a constant depth and width of 150 ηm is used as the simple straight channel of the "Conventional Example".

This shows that the velocity of the reaction solution can be controlled by adjusting the structural design of the channel 100, and that the reaction solution can be fed at a constant velocity. Note that for both the present invention and the conventional example, the simulation values and the measured values are roughly the same, as illustrated in FIG. 7.

With the microfluidic device 1 according to the present embodiment, at least the portion of the channel 100 in the reaction section 110 includes a region having a cross-sectional area that decreases in the feeding direction of the reaction solution.

With this, the feeding of the reaction solution through the channel 100 can be controlled such that the reaction solution flows at a desired velocity, making it possible to maintain a constant feed velocity. As such, the time the reaction solution occupies each of the first temperature zone and the second temperature zone can be maintained at a constant value. Thus, chemical reaction of the reaction solution can be increased.

In the present embodiment, since the channel 100 has a tapered structure in particular, the cross-sectional area of the channel 100 monotonically decreases, With this configuration, since pressure loss and capillary pressure can be continually varied, the reaction solution can be fed at an even more constant velocity.

Moreover, in the present embodiment, the region where the cross-sectional area of the channel 100 decreases is the entire portion of the channel 100 in the reaction section 110. In other words, from the point of entrance into the reaction section 110 to the point of exit from the reaction section 110, the channel 100 gradually decreases in cross-sectional area. In the present embodiment, the width of the channel 100 gradually narrows. However, the entire portion of the channel 100 in the reaction section 100 is not required to have a decreasing cross-sectional area; even with a portion of the channel 100 decreasing in cross-sectional area, the reaction solution can be controlled to flow at a desired velocity, making it possible to maintain a constant feed velocity. Moreover, the rate at which the channel width decreases with respect to the channel length is, for example, 0.05 μm/mm to 0.2 μm/mm. In "Present Invention" in FIG. 7, the rate is approximately 0.1 μm/mm.

Moreover, in the present embodiment, a solution including a target nucleic acid is used as the reaction solution, and the channel 100 alternately passes through the first temperature zone and the second temperature zone repeatedly. Thus, since the reaction efficiency of the reaction solution increases by making the feed velocity constant, a highly efficient PCR by flow can be achieved. Stated differently, highly efficient nucleic acid amplification can be achieved.

Moreover, in the present embodiment, in the region where the cross-sectional area of the channel 100 decreases, the channel 100 has a constant depth. With this, the channel 100 can be easily formed by, for example, etching. Furthermore, since the channel 100 has a constant depth, when taking optical measurements by scanning laser light across the channel 100, the length of the measurement light path can be kept constant, which increases measurement accuracy. This makes it possible to, for example, accurately calculate the amplification amount of nucleic acid.

Moreover, in the present embodiment, since the reaction solution is fed through the channel 100 by capillary force, the reaction solution can be advanced through the channel 100 without the use of an external pump such as a syringe pump. Consequently, the feeding of the reaction solution can be performed easily and at low cost. For example, when a solution including target nucleic acid is used as the reaction solution, nucleic acid amplification of the target nucleic acid can be performed easily and at low cost.

Variations

Hereinafter, variations of the microfluidic device according to the above embodiment will be described.

(Variation 1)

Figure 8A:
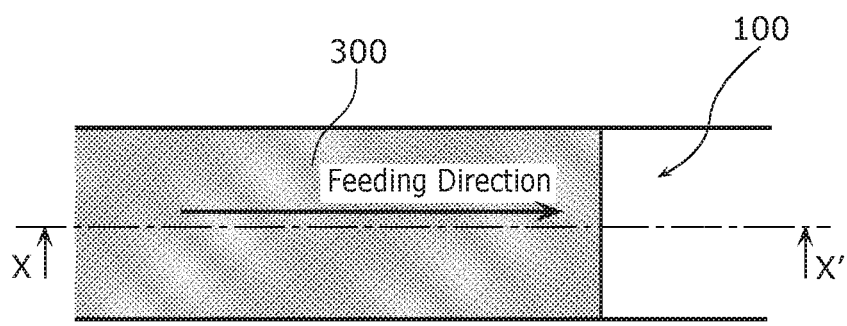
FIG. 8A is an enlarged plan view of a relevant section of a channel in a microfluidic device according to Variation 1 of the present invention.
Figure 8B:
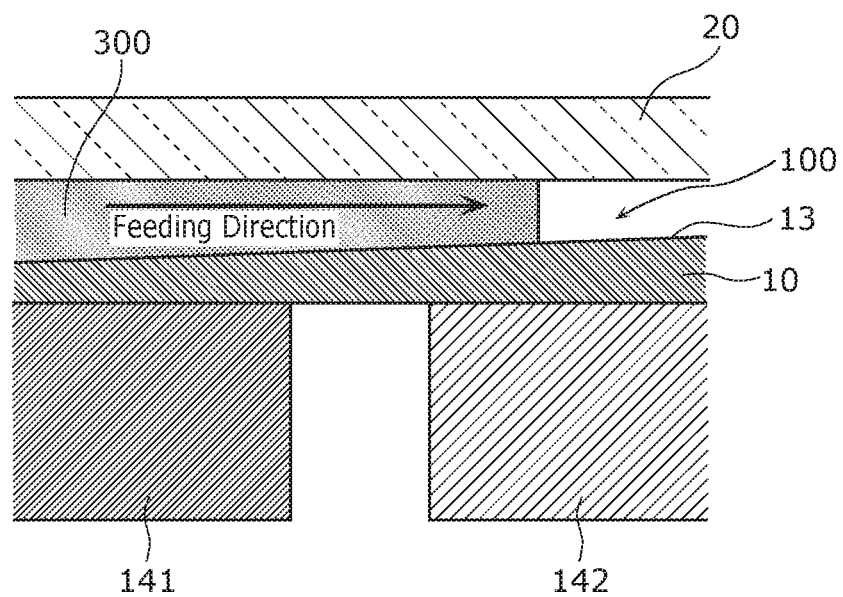
FIG. 8B is a cross sectional view of a channel in a microfluidic device according to Variation 1 of the present invention, taken at line X-X' in FIG. 8A.

FIG. 8A is an enlarged plan view of a relevant section of the channel in the microfluidic device according to Variation 1 of the present invention, and FIG. 8B is a cross sectional view of the channel in the microfluidic device according to Variation 1, taken at line X-X' in FIG. 8A.

With the microfluidic device according to the present variation, similar to the microfluidic device 1 according to the above embodiment, the portion of the channel 100 in the reaction section 110 includes a region having a cross-sectional area that decreases in the feeding direction of the reaction solution 300.

The microfluidic device according to the present variation differs from the microfluidic device 1 according to the above embodiment in that the depth of the channel 100 is constant and the width gradually decreases so as to give the channel 100 a tapered structure in the above embodiment, whereas the width of the channel 100 is constant and the depth gradually decreases so as to give the channel 100 a tapered structure in the present variation.

More specifically, as illustrated in FIG. 8A and FIG. 8B, the channel 100 has a depth that tapers in the feeding direction and a constant width.

With the microfluidic device according to the present variation, similar to the microfluidic device 1 according to the above embodiment, a region having a cross-sectional area that decreases in the feeding direction of the reaction solution 300 is included.

With this, since the reaction solution 300 can be fed through the channel 100 at a constant velocity, the time the reaction solution 300 occupies each of the first temperature zone and the second temperature zone can be maintained at a constant value. Thus, the chemical reaction efficiency of the reaction solution 300 can be increased.

(Variation 2)

Figure 9:
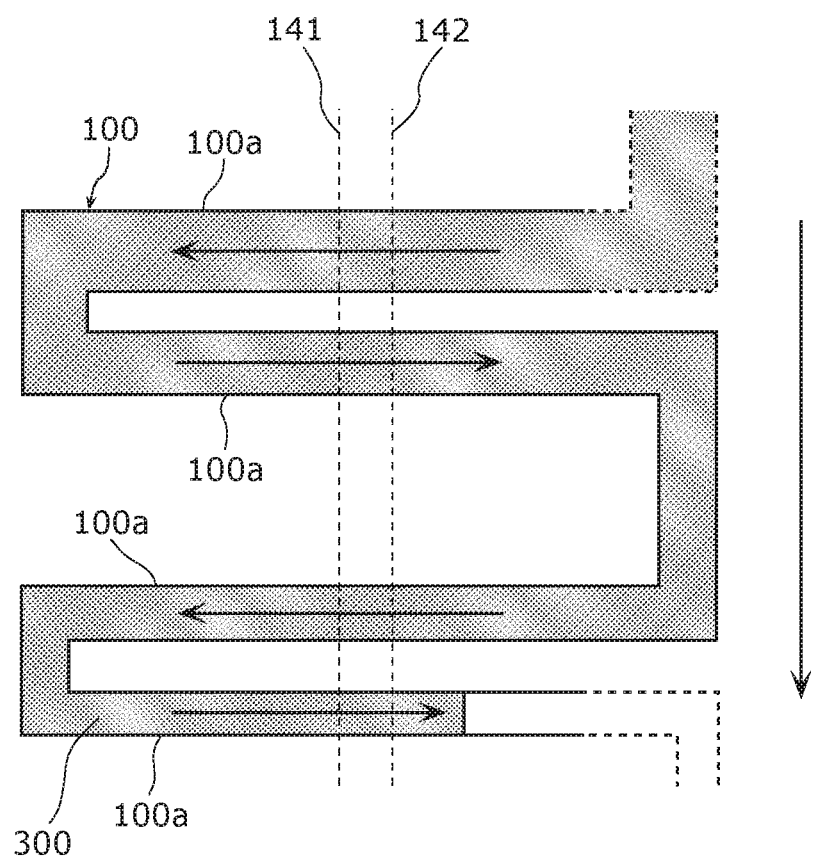
FIG. 9 is an enlarged plan view of a channel in a microfluidic device according to Variation 2 of the present invention.

FIG. 9 is an enlarged plan view of a channel in the microfluidic device according to Variation 2 of the present invention.

With the microfluidic device according to the present variation, similar to the microfluidic device 1 according to the above embodiment, the portion of the channel 100 in the reaction section 110 includes a region having a cross-sectional area that decreases in the feeding direction of the reaction solution.

The microfluidic device according to the present variation differs from the microfluidic device 1 according to the above embodiment in that the cross-sectional area of the channel 100 monotonically decreases in the above embodiment, whereas the cross-sectional area of the channel 100 decreases in a step-wise fashion in the present variation.

More specifically, as illustrated in FIG. 9, the width of the plurality of line-shaped main channels 100a in the channel 100 decreases with each line in the feeding direction of the reaction solution 300. Note that the width and depth of each individual line of the main channel 100a remains constant. With this, the cross-sectional area of the channel 100 decreases in the feeding direction in a step-wise fashion with each line.

The same advantageous effects as the microfluidic device 1 according to the above embodiment can be achieved with the microfluidic device according to the present variation. In other words, the feeding of the reaction solution 300 through the channel 100 can be controlled such that the reaction solution 300 flows at a desired velocity, making it possible to maintain a constant feed velocity. Thus, the time the reaction solution 300 occupies each of the first temperature zone and the second temperature zone can he maintained at a constant value, and the chemical reaction efficiency of the reaction solution 300 can be increased.

Moreover, in the present variation, since the channel 100 is formed in straight lines, the design and formation of the channel 100 is simpler than when a tapered structure is used. Furthermore, since the channel 100 has a constant depth in the present variation, when taking optical measurements by scanning laser light across the channel 100, the length of the measurement light path can be kept constant, which increases measurement accuracy.

(Variation 3)

Figure 10A:
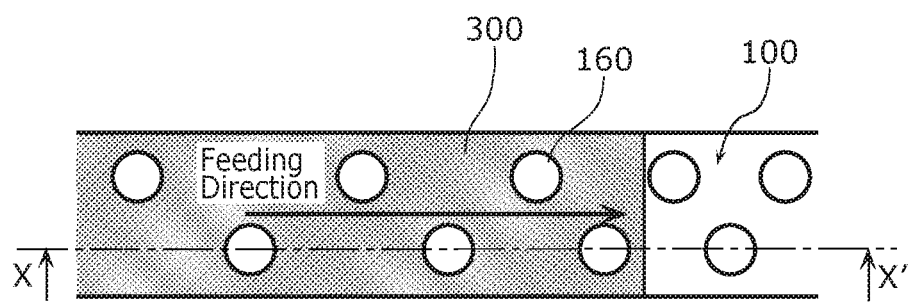
FIG. 10A is an enlarged plan view of a relevant section of a channel in a microfluidic device according to Variation 3 of the present invention.
Figure 10B:
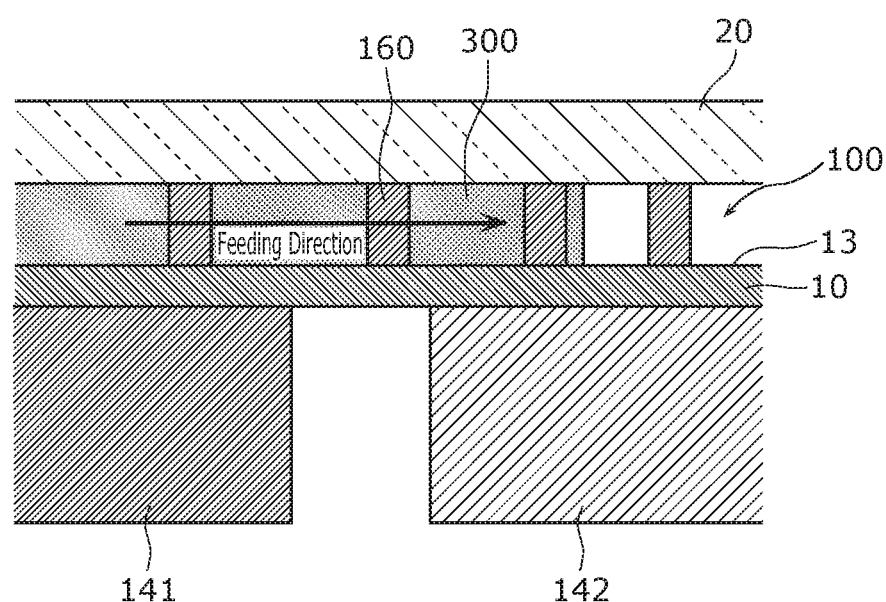
FIG. 10B is a cross sectional view of a channel in a microfluidic device according to Variation 3 of the present invention, taken at line X-X' in FIG. 10A.

FIG. 10A is an enlarged plan view of a relevant section of the channel in the microfluidic device according to Variation 3 of the present invention, and FIG. 10B is a cross sectional view of the channel in the microfluidic device according to Variation 3, taken at line X-X' in FIG. 10A.

With the microfluidic device according to the present variation, similar to the microfluidic device 1 according to the above embodiment, the portion of the channel 100 in the reaction section 110 includes a region having a cross-sectional area that decreases in the feeding direction of the reaction solution 300.

The microfluidic device according to the present variation differs from the microfluidic device 1 according to the above embodiment in that the cross-sectional area of the channel 100 decreases by giving the channel 100 a tapered structure in the above embodiment, whereas the cross-sectional area of the channel 100 is adjusted with pillars 160 in the present variation.

More specifically, as illustrated in FIG. 10A and FIG. 10B, a plurality of cylindrical pillars 160 are disposed upright in the channel 100. With this, the channel cross-sectional area of the region in which the pillars 160 are disposed can be made to be smaller than the channel cross-sectional area of the region in which the pillars 160 are not disposed.

The same advantageous effects as the microfluidic device 1 according to the above embodiment can be achieved with the microfluidic device according to the present variation. In other words, the feeding of the reaction solution 300 through the channel 100 can be controlled such that the reaction solution 300 flows at a desired velocity, making it possible to maintain a constant feed velocity. Thus, the time the reaction solution 300 occupies each of the first temperature zone and the second temperature zone can be maintained at a constant value, and the chemical reaction efficiency of the reaction solution 300 can be increased.

Moreover, like in the present variation, providing the pillars 160 makes it possible to increase the diffusion of the sample and the reagent in the reaction solution 300.

(Variation 4)

Figure 11:
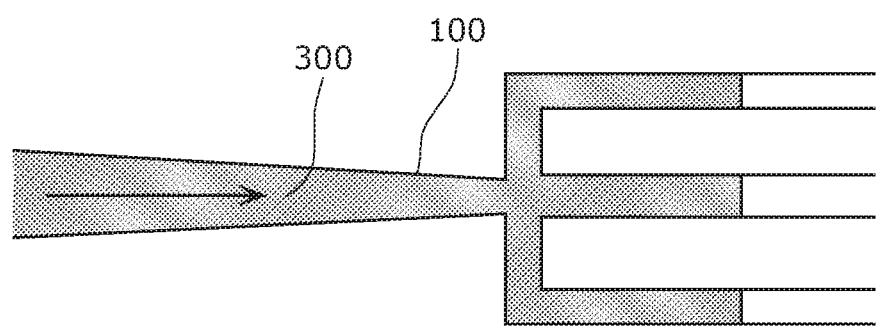
FIG. 11 is an enlarged plan view of a channel in a microfluidic device according to Variation 4 of the present invention.

FIG. 11 is an enlarged plan view of a channel in the microfluidic device according to Variation 4 of the present invention.

In the microfluidic device according to the present variation, a portion of the channel 100 is divided into branches. More specifically, as illustrated in FIG. 11, the tip of the channel 100 having a tapered structure is divided into three branches.

By dividing a portion of the channel 100 into branches in this manner, the feed velocity of the fluid front (front portion) of the reaction solution 300 can be controlled and additionally the feed velocity of the internal portion of the reaction solution 300 can be controlled.

(Variation 5)

Figure 12:
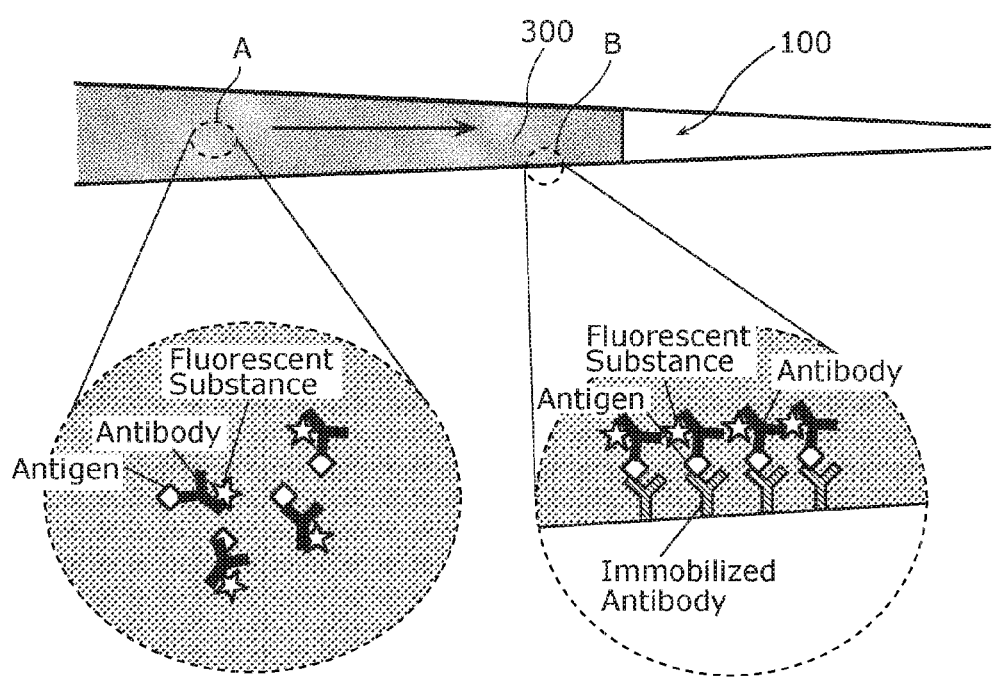
FIG. 12 is an enlarged plan view of a channel in a microfluidic device according to Variation 5 of the present invention.

FIG. 12 is an enlarged plan view of a channel in the microfluidic device according to Variation 5 of the present invention.

In the above embodiment and variations, the microfluidic device is exemplified as being applicable to a nucleic acid amplification device for carrying out a PCR method, but the microfluidic device according to the above embodiment and variations may be applied to a sensor device for detecting an analyte. For example, the microfluidic device can be applied to a sensor device for carrying out an immunochromatographic method.

In this case, the reaction solution introduced into the microfluidic device includes a bacteria or virus as the analyte, and the microfluidic device detects the analyte included in the reaction solution. Each bacteria and virus has a characteristic DNA. Thus, by designing a primer that targets the characteristic DNA, the microfluidic device can be used as a sensor that detects the type and the amount of a bacteria or virus.

For example, as illustrated in FIG. 12, when specifically detecting the antigen, which is the analyte included in the reaction solution 300, in region A in FIG. 12, an immune reaction occurs between the substance that specifically reacts with the antigen (the antibody) and the antigen, whereby the antigen and the antibody selectively bond to form an immunocomplex. Note that a fluorescent substance for detection in advance may be immobilized in the antibody. Moreover, the reaction solution 300 including the antigen and the antibody may be mixed before being introduced into the microfluidic device and, alternatively, the antibody may be dried and placed in region A in advance.

The reaction solution 300 including an immunocomplex formed by an immune reaction is fed to region B. In region B, the antibody (capture antibody) that specifically reacts with the antigen is prepared in advance and immobilized as an immobilized antibody. The antigen that bonded with the antibody in region A bonds with the immobilized antibody in region B. In other words, the immunocomplex becomes trapped by the immobilized antibody. With this, exclusively when the reaction solution 300 includes an antigen, fluorescence can be observed in region B and the antigen can be detected in the reaction solution 300.

In the present variation, the channel 100 has a tapered structure, and the width in region B is narrowed. With this, since the specific surface area (surface area relative to volume) can be increased, the fluorescent substance can be condensed, making highly sensitive measurement possible. Thus, the efficiency of the chemical reaction of the reaction solution 300 can be increased.

(Other Variations)

Although the microfluidic device according to the present invention have been described based on the above embodiments and variations, the present invention is not limited to the above embodiments and variation.

For example, in the above embodiments and variations, a PCR by flow technique in which the channel 100 in the reaction section 110 is a meandering channel and the reaction solution including the target nucleic acid is repeatedly subjected to temperature change is used, but a PCR technique in which the reaction solution including the target nucleic acid is repeatedly subjected to temperature change may be used instead of a PCR by flow technique. However, in the above embodiments, employing a flow technique yields a more efficient PCR.

Moreover in the above embodiments and variations, the channel 100 is a meandering channel, but the channel 100 is not limited to this example. For example, a configuration is acceptable in which a plurality of high temperature zones (95° C.) and a plurality of low temperature zones (60° C.) may be alternately arranged in a linear shape, and a substrate having a line-shaped channel may be disposed thereon to make the channel alternately pass through the high temperature zone and the low temperature zone.

Moreover, in the above embodiments and variations, the heater unit 140 includes two temperature zones, but the heater unit 140 may include three or more temperature zones of mutually different temperatures. In this case, the channel may be configured such that the reaction solution passes through the plurality of different temperature zones in a cyclic fashion.

Moreover in the above embodiments and variations, the setting of the temperature for each of the plurality of temperature zones was achieved with heat blocks, but a different temperature control component such as a Peltier device may be used to set the temperature.

Moreover in the above embodiments and variations, the reaction solution is fed through the channel 100 by capillary force, but this example is not limiting. For example, a syringe pump may be connected to the channel 100 to feed to the reaction solution. However, feeding the reaction solution by capillary force is easier and costs less.

Various modifications of the exemplary embodiments as well as embodiments resulting from arbitrary combinations of elements of different embodiments conceivable by those skilled in the art are intended to be included within the scope of the present invention as long as they do not depart from the essence of the present invention.

REFERENCE SIGNS LIST 1 microfluidic device
10 first substrate
11 first recessed portion
12 second recessed portion
13 groove
20 second substrate
21 first through-hole
22 second through-hole
100 channel
100a main channel
100b sub channel
100c introduction channel
100d discharge channel
110 reaction section
120 introduction unit
130 discharge unit
140 heater unit
141 first heater block
142 second heater block
160 pillar
210 temperature control unit
300 reaction solution

What is claimed is:

1. A microfluidic device comprising:
a channel through which a reaction solution flows, the channel passing through a reaction section having a plurality of temperature zones set at predetermined different temperatures,
wherein an effective cross-sectional area of the channel across the entirety of the reaction section gradually decreases in a feeding direction of the reaction solution.

2. The microfluidic device according to claim 1, wherein the channel in the reaction section has a tapered structure.

3. The microfluidic device according to claim 2, wherein the channel in the reaction section has a tapered width and a constant depth.

4. The microfluidic device according to claim 1, wherein the effective cross-sectional area of the channel in the reaction section decreases in a step-wise fashion in the feeding direction of the reaction solution.

5. The microfluidic device according to claim 1, wherein the effective cross-sectional area of the channel in the reaction section is gradually decreased via a plurality of pillars disposed in the channel.

6. The microfluidic device according to claim 1, wherein the channel is a meandering channel arranged to pass back and forth through the plurality of temperature zones, and
the reaction solution is subjected to cyclic temperature changes by being fed through the meandering channel.

7. The microfluidic device according to claim 6, further comprising the reaction solution, wherein
the reaction solution includes a target nucleic acid, and
the target nucleic acid is amplified by a polymerase chain reaction as a result of the reaction solution passing through the reaction section of the channel.

8. The microfluidic device according to claim 1, further comprising the reaction solution, wherein
the reaction solution includes one of a bacteria and virus as an analyte, and the microfluidic device detects the analyte included in the reaction solution.

9. The microfluidic device according to claim 8, wherein an antibody that specifically reacts with the analyte is immobilized in the channel.

10. The microfluidic device according to claim 1, wherein a portion of the channel is divided into branches.

11. The microfluidic device according to claim 1, wherein the channel is formed in a substrate, and
the substrate includes one of silicon, resin, and glass.

12. The microfluidic device according to claim 1, wherein the effective cross-sectional area of the channel in the reaction section monotonically decreases.

13. A microfluidic device comprising:
a channel through which a reaction solution flows, the channel passing through a reaction section having a plurality of temperature zones set at predetermined different temperatures, wherein
an effective cross-sectional area of the channel in the reaction section gradually decreases in a feeding direction of the reaction solution such that the cross-sectional area of the channel in the reaction section maintains the reaction solution at a constant velocity as the reaction solution passes through each of the plurality of temperature zones of the reaction section,
the effective cross-sectional area of the channel in the reaction section decreases in a step-wise fashion in the feeding direction of the reaction solution,
the reaction section includes a plurality of lines comprising sections of the channel having different orientations with respect to each other that are arranged in a meandering fashion though the plurality of temperature zones, and
the effective cross-sectional area of the channel in the reaction section decreases in the step-wise fashion with each line in the feeding direction.

14. The microfluidic device according to claim 13, wherein
the channel in the reaction section has a narrower width with each line and a constant depth.

15. A microfluidic device comprising:
a channel through which a reaction solution flows, the channel passing through a reaction section having a plurality of temperature zones set at predetermined different temperatures, wherein
the channel includes, at least in the reaction section, a region where a cross-sectional area decreases in a feeding direction of the reaction solution,
the channel includes, in the reaction section, a region where a cross-sectional area decreases in a step-wise fashion in the feeding direction of the reaction solution,
in the region where the cross-sectional area decreases in a step-wise fashion, the channel includes a plurality of lines comprising sections of the channel having different orientations with respect to each other that are arranged in a meandering fashion through the plurality of temperature zones, and
in the region where the cross-sectional area decreases in a step-wise fashion, the cross-sectional area of the channel decreases with each line in the feeding direction.

* * * * *